United States Patent [19]
Prescott et al.

[11] Patent Number: 5,096,615
[45] Date of Patent: Mar. 17, 1992

[54] SOLID AEROSOL GENERATOR

[75] Inventors: Donald S. Prescott, Shelley, Id.; Robert K. Schober, Midwest City, Okla.; John Beller, Idaho Falls, Id.

[73] Assignee: The United States of America as represented by the United States Department of Energy, Washington, D.C.

[21] Appl. No.: 221,490

[22] Filed: Jul. 19, 1988

[51] Int. Cl.$^5$ .................. C09K 3/30; B05B 1/24
[52] U.S. Cl. ...................... 252/305; 252/314; 55/270; 261/78.2; 261/142; 239/8; 239/13; 239/690; 239/691; 250/288
[58] Field of Search ............ 252/305; 239/8, 13, 239/134, 133, 310, 318, 9, 690, 691; 250/288; 261/78.2, 142

[56] References Cited

U.S. PATENT DOCUMENTS

| 2,416,256 | 2/1947 | Hochberg | 252/305 |
|---|---|---|---|
| 2,437,963 | 3/1948 | Langmuir et al. | 252/305 |
| 2,966,312 | 12/1960 | Wilson, Jr. et al. | 239/318 X |
| 3,009,826 | 11/1961 | Straugn et al. | 239/310 X |
| 3,034,726 | 5/1962 | Péras | 239/133 X |
| 4,125,225 | 11/1976 | Venghiattis | |
| 4,164,057 | 8/1988 | Molter et al. | 239/325 X |
| 4,369,850 | 1/1983 | Skekely | |
| 4,623,706 | 11/1986 | Timm et al. | |
| 4,667,100 | 5/1987 | Lagna | 250/282 |
| 4,735,364 | 4/1988 | Marchant | 239/691 X |
| 4,794,086 | 12/1988 | Kasper et al. | 436/36 |
| 4,801,411 | 1/1989 | Wellinghoff et al. | 239/3 X |

FOREIGN PATENT DOCUMENTS

| 234841 | 9/1987 | European Pat. Off. | 239/690 |
|---|---|---|---|
| 958100 | 5/1964 | United Kingdom | 239/690 |
| 2140711 | 12/1984 | United Kingdom | 239/690 |

OTHER PUBLICATIONS

Aerosols Sci., Med. Technol.—Aerosols Ind. Processes—Conf., S. V. Boyd, 1981, pp. 247-252.

Primary Examiner—Robert L. Stoll
Assistant Examiner—John M. Covert
Attorney, Agent, or Firm—Helen S. Cordell; John M. Albrecht; William R. Moser

[57] ABSTRACT

An improved solid aerosol generator used to produce a gas borne stream of dry, solid particles of predetermined size and concentration. The improved solid aerosol generator nebulizes a feed solution of known concentration with a flow of preheated gas and dries the resultant wet heated aerosol in a grounded, conical heating chamber, achieving high recovery and flow rates.

9 Claims, 1 Drawing Sheet

FIG. 1
FIG. 2
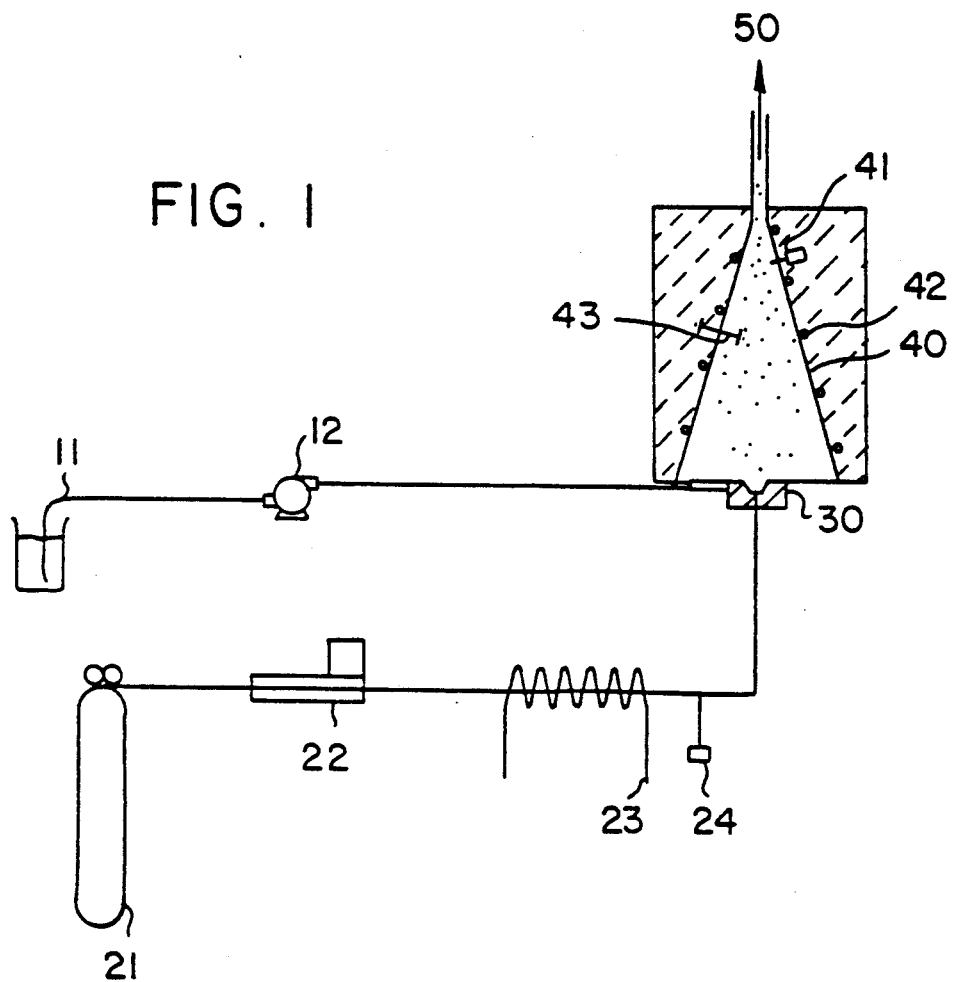
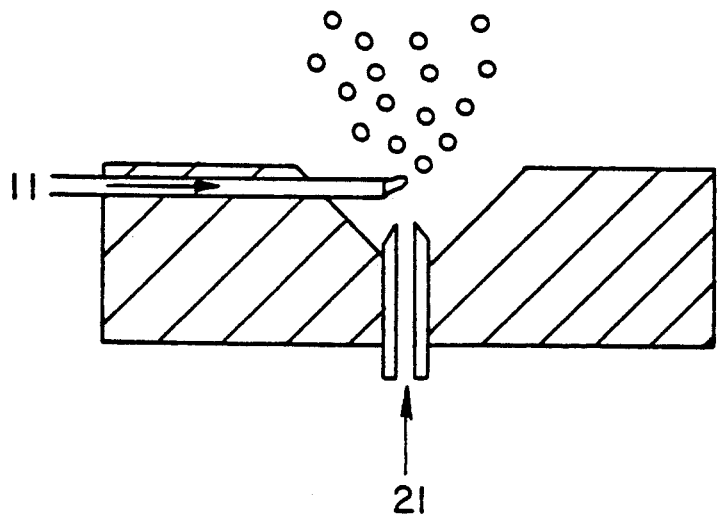

SOLID AEROSOL GENERATOR

CONTRACTUAL ORIGIN OF THE INVENTION

The United States Government has rights in this invention pursuant to Contract No. DE-AC07-76ID01570 between the U.S. Department of Energy and EG&G Idaho, Inc.

BACKGROUND OF THE INVENTION

This invention relates to a solid aerosol generator and more particularly to an improved apparatus for the generation of dry solid particles of minute size and predetermined concentration.

Laser spectrometers, condensation nuclei counters and other instruments are used to measure extremely low concentrations of micron size particles. Calibration of these instruments is accomplished using particle generators capable of producing calibration aerosols, which are colloidal systems of very finely divided liquid or solid particles dispersed in and surrounded by a gas. Aerosol generators may produce suspended particles as small as 0.1 micron, or one-billionth of a meter.

Depending upon the use to which aerosols will be put, it is often desirable to control the size, concentration and rate of production of the particles.

It is an object of this invention to provide an improved dry solid aerosol generator which achieves more than 90% efficiency in converting dissolved solids to solid aerosols.

It is another object of this invention to provide an improved dry solid aerosol generator which produces an adjustable, controllable flow rate, and can achieve flow rates as high as 10 liters/minute.

Additional objects, advantages and novel features of the invention will become apparent to those skilled in the art upon examination of the following and by practice of the invention.

SUMMARY OF THE INVENTION

To achieve the foregoing and other objects, this invention comprises a novel improved solid aerosol generator used to produce a gas borne stream of dry, solid particles. The improved solid aerosol generator comprises a device for heating a flow of gas, nebulizing a feed solution of known concentration with said heated flow of gas, and drying the resultant wet heated aerosol in a grounded, conical heating chamber.

BRIEF DESCRIPTION OF THE DRAWINGS

The present invention is illustrated in the accompanying drawings where:

FIG. 1 is a schematic of the apparatus of the improved aerosol generator.

FIG. 2 is a schematic of the air nebulizer, used to convert a feed solution into a wet aerosol.

DETAILED DESCRIPTION OF THE INVENTION

Referring to the drawings, FIG. 1 is a schematic of the apparatus of the improved aerosol generator. A liquid feed solution 11 is prepared, combining a solute with a solvent. A pump 12 moves the feed solution 11 at a controlled rate to the nebulizer 30.

Simultaneously, compressed air or other gas 21 is fed through tubing into a mass flow controller 22 which maintains the flow of the gas at the required flow rate. From there the gas flows into an inline heater 23 where the gas is heated to the required temperature. A thermocouple 24 monitors the temperature of the gas 21 and provides information to the heater 23, such that the heater 23 is automatically adjusted, maintaining the temperature of the gas 21 at the required temperature.

In the nebulizer 30, the heated gas 21 flows past the stream of feed solution 11, nebulizing the stream and producing a wet heated aerosol. The aerosol is directed into a heated spray chamber 40, where the aerosol is quickly dried into a gas borne stream of solid particles 50.

FIG. 2 depicts in greater detail the nebulizer 30. In the preferred embodiment, the feed solution 11 is moved by a syringe pump 12, in a continuous flow, without pulsations. The heated gas 21 flows vertically, and passes adjacent to the stream of feed solution 11, nebulizing the stream and producing an aerosol. The aerosol moves into the heated spray chamber 40, and the aerosol is then dried from the action of the heated gas 21 and the flow up through the heated spray chamber 40. The spray chamber 40 is designed as a cone so that little or no aerosol is lost to the walls of the chamber, the conical shape impeding the flow of the aerosol as little as possible. Grounding of the chamber through the ground 43 further enhances the unimpeded flow and discourages clinging of the aerosol to the chamber 40 walls. A thermocouple 41 monitors the temperature within the spray chamber 40 and provides the information for the heating coils 42 to maintain a substantially constant temperature in the chamber 40. The dry aerosol 50 then flows from the top of the spray chamber 40 where it can be utilized.

In the preferred embodiment, the improved solid aerosol generator is used to produce calibration gas streams for measurement of the presence of alkali such as sodium chloride and potassium chloride in waste streams. Feed solutions 21 are prepared with concentrations shown in Table 1 following:

TABLE 1

| ALKALI CONCENTRATION OF CALIBRATION SOLUTION (ppm) | SOLUTION FEED RATE (ml/min) | ALKALI CONCENTRATION OF CALIBRATION GAS STREAM (ppb wt/wt) |
|---|---|---|
| BLANK | 0.3 | 0.0 |
| 1 | 0.1 | 8.81 |
| 1 | 0.3 | 25.97 |
| 1 | 1.0 | 81.63 |
| 30 | 0.1 | 264.32 |
| 30 | 0.3 | 779.22 |
| 30 | 1.0 | 2448.98 |
| 1000 | 0.1 | 8810.57 |
| 1000 | 0.3 | 25974.03 |
| 1000 | 1.0 | 81632.65 |

Nitrogen gas 21 is preheated to a temperature of 200°±5° C. and is controlled by the mass flow controller 22, yielding a rotameter reading of 46 at 20 psig. The wall temperature of the heating chamber 40 is also maintained at 200°±5° C.

The alkali concentration values for the calibration gas stream 50 are calculated with the assumption of 100% nebulization efficiency and with respective corrections for the different contributions of water for different solution feed rates. For example, the typical nitrogen flow for calibration (9 standard liters/minute) contributes 28*(9/22.4) grams of nitrogen to the calibration gas stream and a calibrating solution fed at one ml/min contributes one gram/min of water vapor to the calibration gas stream. The concentration of the alkali elements in the calibration gas stream is given by:

alkali concentration in gas (ppb wt/wt) =

$$\frac{[\text{alkali concentration of solution (ppb)}] \cdot [\text{solution feed rate (ml/min)}]}{[\text{nitrogen flow rate (std l/min)}] \cdot [28/22.4] + [\text{solution feed rate (ml/min)}]}$$

Table 1 shows suggested solutions 11 and feed rates, and the corresponding calibration gas stream 50 calibrations.

In an alternate embodiment, again referring to FIG. 1, the size and concentration of the solid particles in the dry aerosol 50 can be controlled by correlating four variables: the flow rate and concentration of the solution 11, as determined by premixture and the pump 12, and the flow rate and temperature of the preheated gas 21, as determined by the mass flow controller 22 and thermostat 24. This instrument thus serves the purpose of providing a calibration aerosol where size as well as concentration of the solid particles is of interest.

The proportion of the original solid which is recovered as a solid aerosol using the present invention is exceptionally high compared to recovery using aerosol generators of the prior art. This invention achieves an efficiency of 90 to 100% recovery. Prior art aerosol generators are designed for the production of solid aerosols used as samples for quality testing, or other applications for which recovery of the original solute is inconsequential, and typically only 1 to 3% of the original solute is recovered.

The present invention also achieves a very high flow rate, 10 liters/minute, compared to the prior art's typical flow rate of one liter/minute.

The advantages of the present invention result from its unique design characteristics aimed primarily at reducing the residence time of the wet aerosol in the drying chamber 40, and thereby minimizing loss due to caking on the walls of the drying chamber 40.

The gas 21 is preheated before mixing with the feed solution 11 and forming a wet heated aerosol. Preheating eliminates the need to raise the temperature of the aerosol before it is dried, thereby reducing the residence time of the aerosol in the drying chamber 40.

The drying chamber 40 is conical and the wet heated aerosol proceeds from the large end of the cone toward the narrowing end of the cone. Drying occurs primarily in a large area, where collision between the aerosol and the walls of the drying chamber 40 is minimal. The stream of aerosol is then gradually reduced in the narrowing end of the cone, encouraging free flow through the exit point rather than caking on the walls of the chamber 40.

The chamber 40 is constructed of stainless steel or other suitable material and is grounded. Experimentation has shown that charge builds up on the walls of a glass or other ungrounded chamber, encouraging clinging of the aerosol to the walls and loss of solid due to caking.

The heated gas 21 is directed to flow vertically rather than horizontally, passing adjacent to the stream of feed solution 11, nebulizing the stream and producing an aerosol. Nebulizers directing the gas 21 horizontally allow the gas 21 to backtrack on itself, causing uneven nebulization and clogging.

A syringe pump 12 provides a continuous flow of feed solution 11, without pulsations. Air nebulizers of the prior art typically employ Bernoulli principles, providing inconsistent streams with a flow rate of only one liter/minute.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

The embodiments of this invention in which an exclusive property or privilege is claimed are defined as follows:

1. A method for preparing a stream of dry, solid particles comprising:
   heating a flow of gas,
   directing said heated flow of gas adjacent to a stream of solute in a solvent, nebulizing said solute in a solvent and said heated flow of gas, and and, forming an aerosol of said gas, solute and solvent,
   drying said wet heated aerosol in a grounded, conical heating chamber to form a gas borne stream of dry, solid particles.

2. A method of providing a stream of dry solid particles of minute size and consistent concentration comprising:
   preparing a feed solution comprising a solute in a solvent of predetermined concentration,
   nebulizing a mixture of said feed solution and preheated gas to form a wet heated aerosol, and
   drying said wet heated aerosol in a grounded, conical heating chamber to provide a gas borne stream of dry solid particles of consistent concentration, based upon the concentration of the feed solution.

3. A method for preparing a stream of dry solid particles of predetermined size and predetermined concentration comprising:
   preparing a feed solution comprising a solute in a solvent of predetermined concentration,
   nebulizing said feed solution with a flow of preheated gas, flowing at a predetermined rate and at a predetermined temperature to form a wet heated aerosol,
   and drying said wet heated aerosol in a grounded, conical heating chamber.

4. A dry aerosol generator comprising:
   means for providing a preheated flow of gas, and a stream of feed solution comprised of a solute in a solvent in predetermined concentration,
   means for nebulizing a mixture of said preheated flow of gas and said feed solution to form a wet heated aerosol,
   a grounded, conical drying chamber for receiving said wet heated aerosol and,
   means for heating said drying chamber to a substantially constant temperature sufficient to vaporize said solvent and to produce a gas borne stream comprised almost exclusively of dry, solid particles.

5. The dry aerosol generator of claim 4 wherein said means for providing said stream of feed solution includes a pump moving said feed solution in a continuous flow, without pulsations.

6. The dry aerosol generator of claim 5 wherein said pump is a syringe pump.

7. The dry aerosol generator of claim 5 wherein said means for providing said stream of feed solution includes controlling the rate of flow of said stream.

8. The dry aerosol generator of claim 4 wherein said means for nebulizing said mixture includes means for directing said flow of gas vertically and adjacent to said stream of feed solution.

9. The dry aerosol generator of claim 8 wherein said wet heated aerosol proceeds vertically within said drying chamber, and from the large end to the narrowing end of said drying chamber.

* * * * *